(12) United States Patent
Chazard

(10) Patent No.: US 6,602,870 B2
(45) Date of Patent: Aug. 5, 2003

(54) ORAL DOSAGE FORM FOR ADMINISTRATION OF THE COMBINATION OF TEGAFUR, URACIL, FOLINIC ACID, AND OXALIPLATIN AND METHOD OF USING THE SAME

(75) Inventor: Michel Chazard, Paris (FR)

(73) Assignee: Bristol-Myers Squibb Company, Princeton, NJ (US)

( * ) Notice: Subject to any disclaimer, the term of this patent is extended or adjusted under 35 U.S.C. 154(b) by 22 days.

(21) Appl. No.: 09/800,675

(22) Filed: Mar. 7, 2001

(65) Prior Publication Data

US 2002/0045632 A1 Apr. 18, 2002

Related U.S. Application Data

(60) Provisional application No. 60/231,147, filed on Sep. 8, 2000, and provisional application No. 60/187,842, filed on Mar. 8, 2000.

(51) Int. Cl.$^7$ .............. A61K 31/50; A61K 31/525
(52) U.S. Cl. .............. 514/249; 514/251; 514/274; 514/922
(58) Field of Search ............... 514/249, 251, 514/274, 922

(56) References Cited

U.S. PATENT DOCUMENTS

| 4,328,229 A | 5/1982 | Fujii et al. |
| 5,534,513 A | 7/1996 | Junji et al. |

OTHER PUBLICATIONS

P.M. Hoff et al., Oncology (Jul. 1999) 13 (7 Suppl. 3) p. 48–50.
M.E. Royce et al., Curr. Opin. Oncol. (1999), 11(4), 299–304.
C. Punt, Cancer (N.Y.) (1998), 83(4), p. 679–689.
E. Van Cutsem, Curr. Opin. Oncol. (United States) Jul. 1999, 11(4), p. 312–317.
E. Van Cutsem, Hepatogastroenterology (Greece) Mar.–Apr. 1999, 46(26) p. 709–716.
W. Scheithauer, Onkologie (Germany) 1999, 22/5, p. 372–373.
M. Royce, Expert Opinion on Investigational Drugs (United Kingdom), 1999, 8/10, p. 1639–1652.
J. Waters, Digestion (Switzerland), 1997, 58/6, p. 508–519.
C. Louvet, Proceedings of the American Association for Cancer Research Annual Meeting, 40, p. 292, Mar. 1999 [abstract 1940].
F. Levi & L. Dagliotti, Proc. Am. Soc. Clin. Oncol. 1997, 16:266a [abstract 945].
S.Giacchetti, Proc. Am. Soc. Clin. Oncol. 1997, 16:229a [abstract 805].
A. de Gramont, Eur. J. Cancer, 1997, 33, p. 214–219.
F. Levi, Cancer, 1992, 69, p. 893–900.
A. de Gramont, Proc. Am. Soc. Clin. Oncol. 34$^{th}$ Annual Meeting, Los Angeles CA, USA (1998) [abstract 985].
T. Andre, Ann. Oncol., (1998)9, p. 1251–1253.
R. Pazdur, Proc. Am. Soc. Clin. Oncol., 35$^{th}$ Annual Meeting, Atlanta Ga, USA (1999) [abstract 1009].
R. Smith, Oncology, 13, No. 7, Supplement No. 3, (1999), p. 44–47.
Hoffman et al.,Oncology, vol. 13, No. 7, Supplement No. 3 (1999) XP001021477 (Abstract) p. 126; Table 1.

*Primary Examiner*—Frederick Krass
(74) *Attorney, Agent, or Firm*—Maureen Gibbons

(57) ABSTRACT

This invention provides a dosage form and a method of administering an anti-tumor composition comprising tegafur, uracil and folinic acid to potentiate the coadministration of oxaliplatin.

9 Claims, 2 Drawing Sheets

ORAL DOSAGE FORM FOR ADMINISTRATION OF THE COMBINATION OF TEGAFUR, URACIL, FOLINIC ACID, AND OXALIPLATIN AND METHOD OF USING THE SAME

RELATED APPLICATIONS

This application claims the benefit under 35 §119(e) of U.S. Provisional Application Ser. Nos. 60/231,147, filed Sep. 8, 2000 and 60/187,842, filed Mar. 8, 2000.

FIELD OF THE INVENTION

The present invention is directed to an oral dosage form for administration to a warm blooded animal of the combination of tegafur, uracil, and folinic acid to potentiate coadministered oxaliplatin for the treatment of tumors.

BACKGROUND OF THE INVENTION

5-Fluorouracil (5-FU) is a known anti-tumor agent. The combination of 5-fluorouracil and folinic acid is a known treatment for colorectal cancer. Tegafur (1-(2-tetrahydrofuryl)-5-fluorouracil) is a prodrug of 5-fluorouracil. In vivo, 5-fluorouracil is rapidly inactivated by the enzyme dihydropyridine dehydrogenase (DPD). Uracil competitively inhibits DPD metabolism of 5-FU generated from tegafur. Thus, coadministration of uracil with tegafur results in higher exposures of active 5-FU as compared to tegafur alone. It is known that 5-fluorouracil cannot be administered orally.

U.S. Pat. No. 4,328,229 discloses an anti-cancer composition containing 1-(2-tetrahydrofuryl)-5-fluorouracil ("tegafur") and uracil. The composition is used for delivery of 5-fluorouracil to a cancer sensitive to 5-fluorouracil in a warm-blooded animal. It is disclosed that the composition can be administered in a variety of dosage forms including an oral dosage form.

U.S. Pat. No. 5,534,513 discloses an anti-tumor composition containing tegafur and uracil in a molar ratio of 1:4. This anti-tumor composition is stated to be further potentiated by the administration of folinic acid or a pharmaceutically acceptable salt thereof. It is disclosed in the '513 patent that the combination can be administered in a variety of dosage forms including an oral dosage form.

Oxaliplatin ($C_8H_{14}N_2O_4Pt$, [(1R, 2R)-1,2-cyclohexanediamine-N,N'][oxalato(2-)-O, O']platinum) is a diaminocyclohexane compound that is known to cause DNA damage of the same sites of adduct formation as does cisplatin. Oxaliplatin has been used to treat various tumors including some that are resistant to cisplatin.

It has been observed that 5-fluorouracil can enhance the activity of oxaliplatin. However, because 5-fluorouracil cannot be administered orally, the mode of administration for this combination therapy requires a more invasive form of administration such as by intravenous injection, and therefore typically requires administration by trained medical personnel.

It would be an advance in the art of treating tumors, especially colorectal cancerous tumors, if a therapy could be developed employing a potentiated form of oxaliplatin through the action of 5-fluorouracil in a convenient dosage form for oral administration.

SUMMARY OF THE INVENTION

The present invention is directed to a dosage form suitable for oral administration to a mammal for the treatment of tumors, especially colorectal tumors, that exhibits a synergistically enhanced effect in combination with oxaliplatin. In particular, there is provided in accordance with the present invention a dosage form suitable for oral administration to a mammal having a tumor comprising an effective amount of each of tegafur, uracil, and folinic acid or a pharmaceutically acceptable salt thereof to a patient undergoing treatment with oxaliplatin, wherein said dosage form is a potentiator of oxaliplatin. In a preferred form of the invention, tegafur and uracil are present in respective amounts sufficient for tegafur to effectively and efficiently convert to 5-fluorouracil. In a particularly preferred form of the invention tegafur and uracil are present in a molar ratio of about 1:4 (hereinafter referred to as "UFT").

There is also disclosed a method of orally administering an anti-tumor effective amount of the combination of tegafur and uracil, preferably as UFT, and folinic acid or a pharmaceutically acceptable salt thereof to a mammal having a tumor who is undergoing oxaliplatin therapy.

The present invention further provides a method for the synergistic treatment of cancer, such as colorectal cancer, which comprises orally administering a synergistically effective amount of tegafur, uracil, and folinic acid or a pharmaceutically acceptable salt thereof, such as calcium folinate, to a mammal undergoing treatment with oxaliplatin.

DETAILED DESCRIPTION OF THE INVENTION

Figure 1:
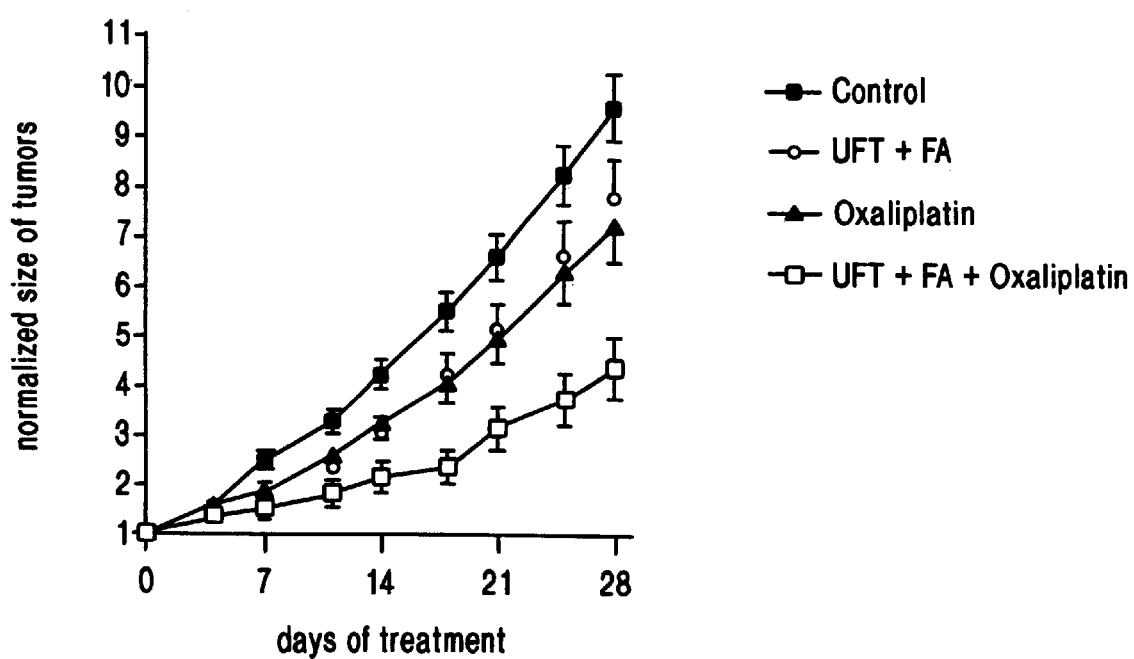
FIG. 1 shows the growth of HT29 tumors following treatment (control, UFT+calcium folinate (FA), oxaliplatin, and UFT+FA+oxaliplatin). The treatment was administered fourteen days after the HT29 xenograft. Tumor size was measured bidimensionally and then normalized according to the size of the tumor before treatment initiation (day 0). Two separate experiments gave comparable results. This figure summarizes the tumor growth in 25 animals per treatment group.

The administration of the combination of tegafur and uracil in amounts sufficient to convert tegafur to 5-fluorouracil (preferably a molar ratio of about 1:4) can be administered orally. It was unexpectedly discovered that oral administration of this combination produced sufficient 5-fluorouracil that potentiation of oxaliplatin would take place despite the inability of 5-fluorouracil itself to be effectively administered orally. This was surprising because the combination of tegafur and uracil is not totally absorbed in the gut. Thus, it was unexpected that there would be a sufficient blood circulating concentration of 5-fluorouracil available to potentiate oxaliplatin.

The oral dosage form used in the present invention provides significant advantages over administering the combination by other modes of administration which are more invasive. In the treatment of tumors, a potential reduction in the cost of therapy because skilled medical personnel are not required to administer the drug and the psychological benefits afforded a patient by taking an oral medication provide significant benefits for patient care.

The dosage forms for all oral administration include tablets, powders, granules, and the like. Excipients and additives which may be used include, but are not limited to, lactose, sucrose, sodium chloride, glucose, urea, starch, calcium, kaolin, crystalline cellulose, salicylic acid, methylcellulose, glycerol, sodium alginate, arabic gum and the like. Conventional binders may be used such as glucose solutions, starch solutions, gelatine solutions, and the like. Disintegrators may be used including, but not limited to, dry starch, sodium alginate, agar powder, calcium carbonate, and the like. Absorbents which may be used include, but are not limited to, starch, lactose, kaolin, bentonite, and the like. Lubricants which may be used include, but are not limited to, purified talc, stearic acid salts, boric acid powder, polyethylene glycol and the like.

Tegafur, uracil, and folinic acid preferably provided as the calcium salt "calcium folinate" are present in the oral dosage form in an amount from about 1 to 70% by weight based on the total weight of the oral dosage form. The dosage of each active ingredient for administration on a daily basis is from about 0.1 to 100 mg/kg/day, preferably about 1 to 30 mg/kg/day for tegafur. The preferred dosage for uracil is from about 1 to 50 mg/kg/day. For UFT, i.e. the 1:4 combination of tegafur and uracil, the dosage is from about 200 to 500 mg/m$^2$/day based on tegafur, preferably from about 250 to 350 mg/m$^2$/day based on tegafur. Folinic acid or a pharmaceutically acceptable salt thereof may be administered in an amount from about 0.1 to 500 mg/kg/day, but preferably is administered as calcium folinate in a fixed dose of about 90 mg/day. The oral dosage form may be administered in a single dose or in divided doses typically up to 3 times a day. Oxaliplatin is typically administered in a non-oral mode of administration, typically intravenously. The dosage may range from 1 to 50 mg/kg/day, preferably about 10 mg/kg/day. Based on body surface area, the dosage may range from 50 to 150 mg/m$^2$/day, preferably about 130 mg/m$^2$/day.

Those of ordinary skill in the art would have the knowledge to adjust the above stated dosage ranges for UFT, folinic acid or a pharmaceutically acceptable salt thereof, and oxaliplatin as needed based on body surface area and/or in the event of toxicity. In accordance with the present invention, the combination of tegafur and uracil (e.g. UFT) results in a sufficient amount of 5-fluorouracil available to potentiate oxaliplatin to improve the availability and potency of oxaliplatin in the treatment of tumors, especially colorectal tumors.

The following examples are exemplary of the claimed invention, but are not intended to limit the invention as encompassed by the full disclosure set forth in.

EXAMPLE 1

This study assessed the in vivo cytotoxic effects of oxaliplatin combined with UFT (tegafur and uracil in a molar ratio of 1:4) plus calcium folinate.

Growth inhibition studies were performed using nude mice transplanted with human HT29 colorectal tumor cell xenografts and 1) not treated (control group), or treated 2) with oral UFT (20 mg/kg/day) and calcium folinate (4 mg/kg/day) for 28 days; 3) intraperitonealy with oxaliplatin (10 mg/kg at day 1), or 4) with a combination of oxaliplatin with UFT and calcium folinate. Tumor measurements were performed twice a week, and animals were sacrificed at day 28. The tumors were excised and weighed. Two separate experiments were performed, for a total number of 25 animals in each group.

Mean tumor weights were 2.89±0.22 g (control); 2.03±0.14 g (oxaliplatin); 2.02±0.21 g (UFT+calcium folinate); and 1.23±0.17 g (oxaliplatin+UFT+calcium folinate). Tumor weight decreases were 30.1% (p<0.05), 29.9% (p<0.05) and 57.5% (p<0.001) for UFT/calcium folinate, oxaliplatin and the combination of oxaliplatin/UFT/calcium folinate, respectively. Adding oxaliplatin to UFT+calcium folinate induced a 39.3% tumor weight decrease as compared to UFT+calcium folinate (p<0.05). This study demonstrated a synergistic effect for the combination of oxaliplatin, UFT and calcium folinate.

UFT was obtained from Bristol-Myers Squibb France (Paris, France); calcium folinate was purchased from Sigma Chemical Co. (St. Louis, Mo.), Oxaliplatin was obtained from Sanofi Recherche France (Paris, France).

Human colorectal cancer HT29 cells, obtained from Dr. J. Fogh (Sloan Kettering Institute for Cancer Research, N.Y.), were cultured in DMEM (Dulbeccos modified Eagle's medium, Eurobio, Paris, France), supplemented with 10% heat-decomplemented fetal bovine serum (Boehringer, Manheim, Germany), 100 U/ml penicillin, 100 μg/ml streptomycin and 8 nM glutamine. Cells were grown at 37° C. in a humidified atmosphere containing 5% $CO_2$. The medium was renewed every 2 days, and the cells were passaged twice a week by trypsin/EDTA to maintain the cells in exponential growth.

Female BALB/c nude (nu+/nu+) aged 6 weeks were maintained in pathogen free state. Human HT29 colorectal xenograft (1×10$^6$ cells) was transplanted sub-cutaneously into the hind limb of each animal. Treatment was initiated 14 days later when the tumor became easily palpable and measurable (mean size of tumor surface=33 mm$^2$).

After tumor occurrence, animals were allocated to four groups: control (group 1), oxaliplatin (group 2), UFT+calcium folinate (group 3), and oxaliplatin+UFT+calcium folinate (group 4). Oxaliplatin was administered intraperitoneally at a dose of 10 mg/kg day 1. UFT (20 mg/kg/day) and calcium folinate (4 mg/kg/day) were daily administered orally from day 1 to day 28.

Two axes (mm) of tumor (the longest axis and the axis perpendicular to the longest axis) were measured with a caliper. Tumor measurements and body weights were recorded twice a week. Repetitive tumor measurements were normalized to that of initial measurement, in order to establish growth curves for each group. For each experiment, the same observer made all measurements to minimize variations. Toxicity was evaluated in terms of body weight ratio ($W_n/W_o$) and mortality; $W_n$ is the body weight measured n days after the initial administration, while $W_o$ is the body weight at the start of administration. Animals were sacrificed 28 days after treatment initiation, thereafter the tumors were excised and weighed. Results are expressed as mean weight (grams)±standard deviation. One specimen of each group was sent to the pathological department. Two consecutive experiments gave similar data, and results represent the average of all data for a total of 25 animals per group. The means of each of the four groups were compared using the one-way analysis of variance. The Barlett's test was used for homogeneity of variances and the Tukey-Kramer multiple comparison test for inter-group comparison. Data analysis was performed using an IBM PC. Statistical analysis and graphs were performed using Instat and Prism software (GraphPad, San Diego, Calif.).

No toxicity was observed in any treatment group: all animals were alive at day 28, and the mean body weight was similar in the four groups (Table 1). Body weight was evaluated in terms of the ratio of body weight measured n days after treatment ($W_n$) as compared to the body weight at the start of treatment ($W_o$). All animals (25 per group) were weighed twice a week. Table 1 indicates the results of body weight ratio at day 28 before sacrificed.

TABLE 1

Mean Body Weight at Day 28

| Group | Body Weight Ratio ($W_n/W_o$) |
|---|---|
| control | 1.02 ± 0.08 |
| UFT + calcium folinate (FA) | 1.02 ± 0.07 |
| oxaliplatin (OXA) | 1.05 ± 0.09 |
| combined treatment (UFT + FA + OXA) | 1.01 ± 0.08 |

Tumor growth as shown in FIG. 1 was slightly inhibited by UFT+calcium folinate (group 3) or oxaliplatin (group 2) as compared to control (group 1) with a decrease of 19% and 24% of tumor size at day 28, respectively. Tumor growth inhibition at day 28 was 54% for combined treatment (group 4) as compared to control, 45% and 40% as compared to UFT+calcium folinate or oxaliplatin alone, respectively.

Figure 2:
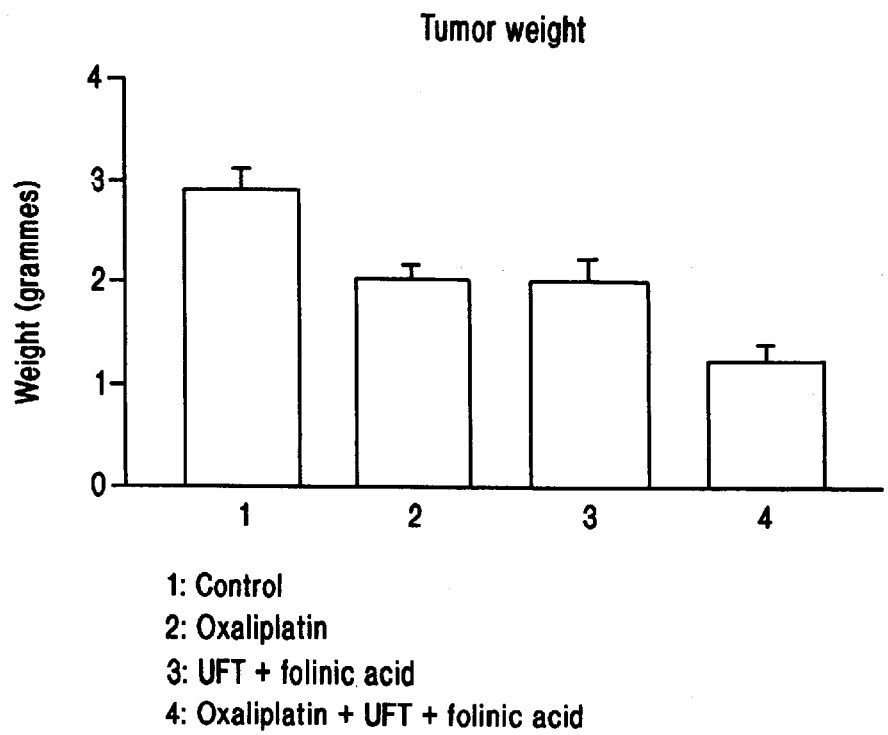
FIG. 2 shows the mean tumor weight after 28 days of treatment for group 1 (control), group 2 (oxaliplatin), group 3 (UFT+calcium folinate), and group 4 (UFT+calcium folinate+oxaliplatin). This figure represents the mean of tumor weight±SEM (25 animals per group).

Mean tumor weights as shown in FIG. 2 were 2.89±0.22 g in the control group; 2.03±0.14 g in the oxaliplatin group; 2.02±0.21 g in the UFT+calcium folinate group; and 1.23±0.17 g in the combined treatment group. Analysis of variance showed that variations among column means were significant (F=12.536; 99 degrees of freedom; p<0.0001). The Barlett test showed that the difference among the standard deviations were not significant (Barlett=6.648; p=0.084). Tumor weight decreases as compared to control were 30% for UFT+calcium folinate (q=4.442; p<0.05), 30% for oxaliplatin (q=4.416; p<0.05) and 58% for combined treatment (q=8.672; p<0.001). Comparison between UFT+calcium folinate and oxaliplatin group showed no statistical difference. Combined treatment induced a tumor weight decrease of 39% (q=4.256; p<0.05) and 39% (q=4.230; p<0.05) as compared to oxaliplatin and UFT+calcium folinate alone, respectively. Pathological examination of the tumors showed no difference between the four groups.

Figure 3:
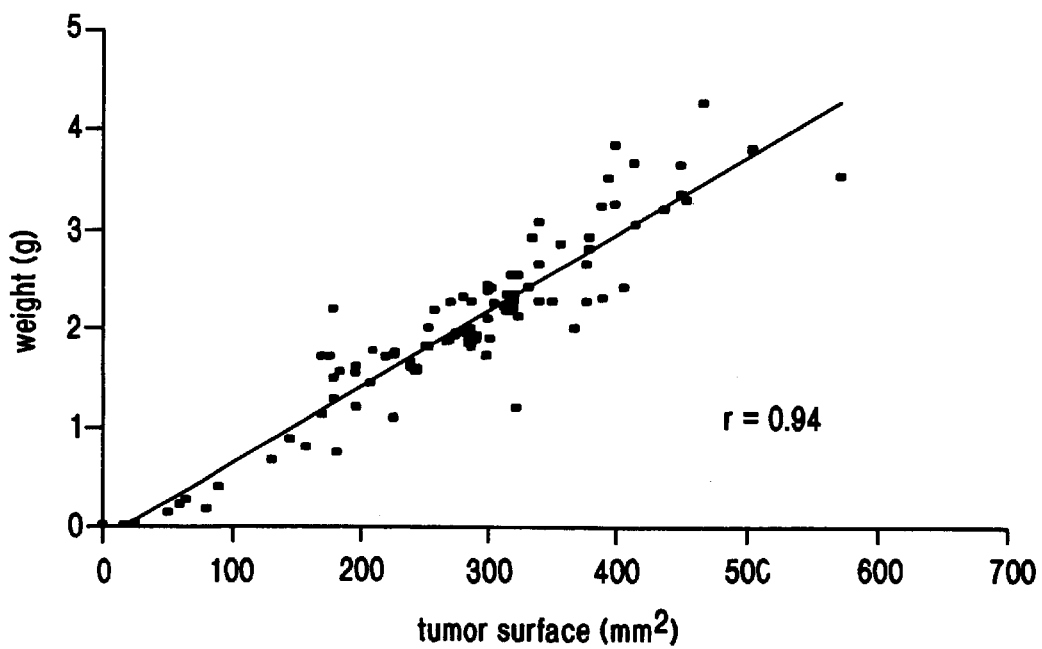
FIG. 3 shows the correlation between tumor surface and tumor weight at the time the animal was sacrificed (r=0.94).

The correlation between tumor size and tumor weight is shown in FIG. 3, which shows a strong correlation (r=0.94) between these two factors. This correlation was done to validate the method of measurement for tumor weight.

EXAMPLE 2

This study assessed the in vivo maximum tolerated dose (MTD), the side effect profile and the dose limiting toxicity (DLT) of oxaliplatin combined with UFT (tegafur and uracil in a molar ration of 1:4) plus calcium folinate.

A standard phase I trial with escalating doses of UFT and oxaliplatin with a fixed dose of calcium folinate at 90 mg/day. Up to six cohorts of three to six patients each are planned. Entry criteria for the study included, but was not limited to, a histological or cytological confirmed metastatic colorectal carcinoma that was not a candidate to curative surgery, no concurrent radiotherapy, no prior chemotherapy for metastatic disease, a World Health Organizaation ("WHO") performance status of 0-2, as described in Miller, A. B. et al., Cancer (1981)11:7–33, the content of which is incorporated herein as if set forth at length, no brain metastatic disease, no evidence of peripheral neuropathy, a Common Toxicity Criteria ("CTC") grade of one or less, as described in CTC version 2, the content of which is incorporated herein as if set forth at length, adequate hematological, renal and hepatic function, and capable of reliable self-medication.

The dosages for UFT, oxaliplatin and calcium folinate for each level are escalated as follows:

| Cohort Level | UFT Dosage (mg/m$^2$/day) | Oxaliplatin Dosage (mg/m$^2$/day) | Calcium Folinate Dosage (mg/day) |
|---|---|---|---|
| 1 | 200 | 100 | 90 |
| 2 | 250 | 100 | 90 |
| 3 | 250 | 115 | 90 |
| 4 | 250 | 130 | 90 |
| 5 | 300 | 130 | 90 |
| 6 | 350 | 130 | 90 |

The treatments were given on a three-week cycle until progressive disease or unacceptable toxicity occurs. UFT and calcium folinate were given orally on days 1–14 of each cycle; oxaliplatin was administered intravenously on day 1 of each cycle.

The study continued to each progessive level until the maximum tolerated dose (MTD) was experienced. The MTD was defined as the dose level at which three or less patients out of six in a cohort experienced no dose limiting toxicity (DLT) at that cycle of treatment. Toxicity was assessed according to the National Cancer Institutes' CTC scale, as set forth above. Dose reductions and delays were protocol-defined. Hematological and peripheral neuropathy toxicities of grade 1 on day 1 were allowed without delay or reduction, but if more severe side effects were observed, the cycle was delayed by one week and the oxaliplatin dosages was reduced. Side effects typically associated with UFT, such as diarrhea, nausea and vomiting, were initially managed symptomatically. If the side effects were persistent and/or if they were assigned a CTC grade of two or higher, the UFT dose was withheld until recovery and then de-escalated by 50 mg/m$^2$. Radiological tumor reassessment was done with a CT scan every three cycles, at the end of treatment and thereafter, every three months or as clinically indicated. Standard WHO response criteria, as described above, were utilized in the evaluations.

To date, 19 patients have been treated up to level 6 (350 mg/m$^2$ of UFT based on tegafur and 130 mg/m$^2$ of oxaliplatin) and no DLT has been observed. 13 patients have been evaluated for treatment efficacy: one patient had a progressive disease after two cycles and withdrew from the study, nine patients achieved a stable disease and three patients had partial responses.

Hematological Toxicity

Hematological toxicity was evaluated weekly (WBC, ANC, platelets, and hemoglobin). Grade 3 anemia occurred in 1 patient at dose level 2. No grade 3/4 neutropenia was observed. No febrile neutropenia was observed.

Non-Hematological Toxicity

| Event per patient (n = 13) | Grade I | Grade II | Grade III | Grade IV |
|---|---|---|---|---|
| Nausea | 10 | 2 | 0 | 0 |
| Vomiting | 2 | 7 | 0 | 0 |
| Diarrhea | 5 | 2 | 1 | 0 |
| Stomatitis | 2 | 0 | 0 | 0 |
| Parasthesia | 9 | 3 | 0 | 0 |
| Asthenia | 4 | 3 | 1 | 0 |
| Hypersensitivity reaction/shock* | 0 | 0 | 1* | 0 |
| Skin disorder | 1 | 0 | 0 | 0 |

*during oxaliplatin infusion

One patient experienced two serious adverse events: asthenia grade III and pneumopathy grade III, both of which were deemed to be unrelated to the treatment. Another patient experienced a pneumopathy grade IV, which was considered to be potentially drug-related. In view of these results, clinical activity has been shown without reaching DLT at the 350 mg/m² UFT and 130 mg/m² oxaliplatin dosages.

What is claimed is:

1. A method for the synergistic treatment of cancer which comprises orally administering a synergistically effective amount of tegafur, uracil, and folinic acid or a pharmaceutically acceptable salt thereof to a mammal undergoing treatment with oxaliplatin.

2. The method according to claim 1 wherein the cancer is colorectal cancer.

3. The method according to claim 1 wherein tegafur and uracil are present in a molar ratio of 1:4 relative to each other, respectively.

4. The method according to claim 1 wherein tegafur is orally administered at a dosage of about 1 to 30 mg/kg/day, uracil is orally administered at a dosage of about 1 to 50 mg/kg/day, and calcium folinate is orally administered at a fixed dosage of about 90 mg/day.

5. The method according to claim 1 wherein the mammal is treated with oxaliplatin at a dosage of about 50 to 150 mg/m²/day.

6. A method for the synergistic treatment of cancer which comprises orally administering a synergistically effective amount of UFT and folinic acid or a pharmaceutically acceptable salt thereof to a mammal undergoing treatment with oxaliplatin.

7. The method according to claim 6 wherein the cancer is colorectal cancer.

8. The method according to claim 6 wherein UFT is orally administered at a dosage of about 200 to 500 mg/m²/day based on tegafur, calcium folinate is orally administered at a fixed dosage of about 90 mg/day, and the mammal is treated with oxaliplatin at a dosage of about 50 to 150 mg/m²/day.

9. The method according to claim 6 wherein UFT is orally administered at a dosage of about 250 to 350 mg/m²/day based on tegafur, calcium folinate is orally administered at a fixed dosage of about 90 mg/day, and the mammal is treated with oxaliplatin at a dosage of about 130 mg/m²/day.

* * * * *